United States Patent
Green et al.

[19]

[11] Patent Number: 6,051,146
[45] Date of Patent: Apr. 18, 2000

[54] METHODS FOR SEPARATION OF PARTICLES

[75] Inventors: Todd Curtis Green, Lakewood; Raymond P. Goodrich, Denver, both of Colo.

[73] Assignee: COBE Laboratories, Inc., Lakewood, Colo.

[21] Appl. No.: 09/009,378

[22] Filed: Jan. 20, 1998

[51] Int. Cl.[7] ................................................. B01D 21/26
[52] U.S. Cl. ......................... 210/782; 210/786; 210/787; 210/789; 435/2; 494/37
[58] Field of Search ................................ 210/782, 787, 210/789, 786, 806; 494/37; 435/2; 604/4, 5, 6

[56] References Cited

U.S. PATENT DOCUMENTS

| | | |
|---|---|---|
| 2,616,619 | 11/1952 | MacLeod . |
| 3,825,175 | 7/1974 | Sartory . |
| 4,091,989 | 5/1978 | Schlutz . |
| 4,187,979 | 2/1980 | Cullis et al. . |
| 4,190,563 | 2/1980 | Bosley et al. . |
| 4,239,729 | 12/1980 | Hasegawa et al. .......................... 422/48 |
| 4,268,393 | 5/1981 | Persidsky et al. ........................ 210/516 |
| 4,269,718 | 5/1981 | Persidsky ................................. 210/787 |
| 4,316,576 | 2/1982 | Cullis et al. . |
| 4,322,298 | 3/1982 | Perisdsky ................................. 210/787 |
| 4,350,283 | 9/1982 | Leonian . |
| 4,393,081 | 7/1983 | Figdor et al. ................................ 435/2 |
| 4,416,654 | 11/1983 | Schoendorfer et al. ................... 494/10 |
| 4,425,112 | 1/1984 | Ito .............................................. 494/18 |
| 4,464,167 | 8/1984 | Schoendorfer et al. ..................... 604/6 |
| 4,540,407 | 9/1985 | Dunn ........................................ 604/292 |
| 4,675,117 | 6/1987 | Neumann et al. ........................ 210/789 |
| 4,680,025 | 7/1987 | Kruger et al. ................................ 604/6 |
| 4,701,267 | 10/1987 | Watanabe et al. ....................... 210/806 |
| 4,708,710 | 11/1987 | Dunn, Jr. .................................... 494/37 |
| 4,708,712 | 11/1987 | Mulzet ....................................... 494/45 |
| 4,798,579 | 1/1989 | Penhasi ...................................... 494/18 |
| 4,808,151 | 2/1989 | Dunn, Jr. et al. ............................ 604/6 |
| 4,851,126 | 7/1989 | Schoendorfer .......................... 210/651 |
| 4,885,137 | 12/1989 | Lork ......................................... 422/140 |
| 4,936,820 | 6/1990 | Dennehey et al. ........................... 494/1 |
| 4,936,998 | 6/1990 | Nishimura et al. ...................... 210/638 |
| 4,939,087 | 7/1990 | Van Wie et al. .................... 435/240.25 |
| 5,078,671 | 1/1992 | Dennehey et al. ......................... 494/27 |

(List continued on next page.)

FOREIGN PATENT DOCUMENTS

| | | |
|---|---|---|
| 057 907 | 8/1982 | European Pat. Off. . |
| 0 214 614 A2 | 3/1987 | European Pat. Off. . |
| 0 323 341 A2 | 7/1989 | European Pat. Off. . |
| 0 406 485 A1 | 1/1991 | European Pat. Off. . |
| 0 408 462 A2 | 1/1991 | European Pat. Off. . |
| 0 419 346 A2 | 3/1991 | European Pat. Off. . |

(List continued on next page.)

OTHER PUBLICATIONS

D.G. Walton et al., Creation of Stable Polyethlene oxide) Surfaces on Poly(methyl methacrylate) Using Blends of Branched and Linear Polymers; Macromolecules 30:6947–6956 (1997).

(List continued on next page.)

*Primary Examiner*—John Kim
*Attorney, Agent, or Firm*—Finnegan, Henderson, Farabow, Garrett & Dunner, L.L.P.

[57] ABSTRACT

A system and method are disclosed for separating particles having different sedimentation velocities. The system includes a fluid chamber for separating the particles form one another. Conduits are provided for flowing liquid carrying particles to the fluid chamber and for mixing the liquid with a diluting liquid. Structure is also provided for separating particles from the liquids after the particles are separated in the fluid chamber. The disclosed methods include forming a saturated fluidized bed of first particles to retain second particles in the fluid chamber. A diluting liquid having a density less than that of the particles is mixed with the liquid carrying particles to reduce overall density of substances in the fluid chamber and thereby reduce Coriolis jetting of liquids in the fluid chamber.

30 Claims, 3 Drawing Sheets

U.S. PATENT DOCUMENTS

| | | | |
|---|---|---|---|
| 5,089,146 | 2/1992 | Carmen et al. | 210/782 |
| 5,100,564 | 3/1992 | Pall et al. | 210/782 |
| 5,213,970 | 5/1993 | Lopez-Berestein et al. | 435/70.4 |
| 5,224,921 | 7/1993 | Dennehey et al. | 494/18 |
| 5,229,012 | 7/1993 | Pall et al. | 210/767 |
| 5,282,982 | 2/1994 | Wells | 210/800 |
| 5,298,171 | 3/1994 | Biesel | 210/739 |
| 5,316,666 | 5/1994 | Brown et al. | 210/85 |
| 5,316,667 | 5/1994 | Brown et al. | 210/85 |
| 5,360,542 | 11/1994 | Williamson, IV et al. | 210/232 |
| 5,362,291 | 11/1994 | Williamson, IV | 494/18 |
| 5,370,802 | 12/1994 | Brown | 210/782 |
| 5,397,479 | 3/1995 | Kass et al. | 210/728 |
| 5,409,813 | 4/1995 | Schwartz | 435/7.24 |
| 5,429,802 | 7/1995 | Hagiwara et al. | 422/48 |
| 5,474,687 | 12/1995 | Van Vlasselaer | 210/782 |
| 5,501,795 | 3/1996 | Pall et al. | 210/508 |
| 5,529,691 | 6/1996 | Brown | 210/512.1 |
| 5,547,591 | 8/1996 | Hagihara et al. | 210/782 |
| 5,549,834 | 8/1996 | Brown | 210/806 |
| 5,580,465 | 12/1996 | Pall et al. | 210/767 |
| 5,587,070 | 12/1996 | Pall et al. | 210/202 |
| 5,607,830 | 3/1997 | Biesel et al. | 435/2 |
| 5,614,106 | 3/1997 | Payrat et al. | 210/767 |
| 5,622,819 | 4/1997 | Herman | 435/4 |
| 5,641,414 | 6/1997 | Brown | 210/782 |
| 5,641,622 | 6/1997 | Lake et al. | 435/2 |
| 5,643,786 | 7/1997 | Cohen et al. | 435/325 |
| 5,674,173 | 10/1997 | Hlavinka et al. | 494/17 |
| 5,722,926 | 3/1998 | Hlavinka et al. | 494/37 |
| 5,906,570 | 8/1999 | Langley et al. | 494/45 |
| 5,913,768 | 8/1999 | Langley et al. | 494/7 |
| 5,939,319 | 8/1999 | Hlavinka et al. | 435/325 |

FOREIGN PATENT DOCUMENTS

| | | |
|---|---|---|
| 2658926 | 6/1978 | Germany . |
| 37 00 122 | 7/1988 | Germany . |
| WO 92/21387 | 12/1992 | WIPO . |
| WO 94/02157 | 2/1994 | WIPO . |
| WO 94/25086 | 11/1994 | WIPO . |
| WO 94/27698 | 12/1994 | WIPO . |
| WO 96/33023 | 10/1996 | WIPO . |
| WO 96/40402 | 12/1996 | WIPO . |
| WO 97/30748 | 8/1997 | WIPO . |
| WO 97/43045 | 11/1997 | WIPO . |

OTHER PUBLICATIONS

Hydrophilic polymer surface prepared with branched additive; C&EN Nov. 17, 1997 p. 30.

Maxim D. Persidsky et al., Separation of Platelet–rich Plasma by Modified Centrifugal Elutriation; Journal of Clinical Apheresis 1:18–24 (1982).

John F. Jemionek et al., Special Techniques for the Separation of Hemopoietic Cells, Current Methodology in Experimental Hematology, 1984, pp. 12–16.

J. Freedman et al., White Cell Depletion of Red Cell and Pooled Random–Donor Platelet Concentrates by Filtration and Residual Lymphocyte Subset Analysis, Transfusion, 1991, vol. 31, No. 5, pp. 433–440.

Nancy M. Heddle et al., The Role of the Plasma from Platelet Concentrates in Transfusion Reactions, The New England Journal of Medicine, vol. 331, No. 10, Sep. 8, 1994, pp. 625–628, 670 and 671.

A. Bruil et al., Asymmetric Membrane Filters for the Removal of Leukocytes From Blood, Journal of Biomed. Materials Research, vol. 25, 1459–1480, 1991.

Sunny Dzik, Leukodepletion Blood Filters: Filter Design and Mechanisms of Leukocyte Removal, Transfusion Medicine Reviews, vol. VII. No. 2, Apr. 1993, pp. 65–77.

Bernard J. Van Wie et al., The Effect of Hematocrit and Recycle on Cell Separations, Plasma Ther. Transfus. Technol. 1986; 7:373–388.

P.D. Drumheller et al., The Effects of RPM and Recycle on Separation Efficiency in a Clinical Blood Cell Centrifuge, Journal of Biomechanical Engineering, Nov. 1987, vol. 109, pp. 324–329.

R.J. Oxford et al., Monitoring and Automated Optimization of a Cell Centrifuge, IEEE/Eighth Annual Conference of the Engineering in Medicine and Biology Society, pp. 925–927 (1986).

R.J. Oxford et al., Interface Dynamics in a Centrifugal Cell Separator, Transfusion, Nov.–Dec., 1988, vol. 28, Nov. 6, pp. 588–592.

A. Tulp et al., A Separation Chamber to Sort Cells and Cell Organelles by Weak Physical Forces, V.A. Sector–Shaped Chamber and Its Application to the Separation of Peripheral Blood Cells, Journal of Immunological Methods 69 (1984), pp. 281–295.

Robert J. Grabske, Separating Cell Populations by Elutriation, pp. 1–8 (undated).

Carl G. Figdor et al., Theory and Practice of Centrifugal Elutriation (CE) Factors Influencing the Separation of Human Blood Cells, Cell Biophysics 5, 105–118 (1983).

P.E. Lindahl, On Counter Streaming Centrifugation in the Separation of Cells and Cell Fragments (1956), pp. 411–415.

C. Almici et al., Counterflow Centrifugal Elutriation: Present and Future, Bone Marrow Transplantation 1993, 12:105–108.

Richard J. Sanderson, Separation of Different Kinds of Nucleated Cells from Blood by Centrifugal Elutriation, Cell Separation Methods and Selected Applications, vol. 1, pp. 153–168.

P.C. Keng et al., Characterization of the Separation Properties of the Beckman Elutriator System, Cell Biophysics 3 (1981), pp. 41–56.

Biofil, Systems for Filtration of Haemocomponents (undated).

Claes, F. Hogman, Leucocyte Depletion of Blood Components, 1994, pp. 1,156–173.

A.S. Buchanan et al., Principle of a Counter–streaming Centrifuge for the Separation of Particles of Different Sizes, Nature, Apr. 24, 1948, pp. 648–649.

"Cost–Effectiveness of Leukocyte Depletion of Blood Components", Presented at the 1993 AABB Meeting Miami Beach, FL.

I. Sniecinski, Prevention of Immunologic and Infectious Complications of Transfusion by Leukocyte Depletion, Prevention of Complications of Transfusion Chapter 18; pp. 202–211.

Benefits of Leukocyte Filtration for Red Cell and Platelet Blood Products, Transfusion Associated CMV (1994), pp. 1–18.

G. Stack et al., Cytokine Generation in Stored Platelet Concentrates, Transfusion, 1994; 34:20–25.

N. M. Heddle et al., A prospectivie study to identify the risk factors associated with acute reactions to platelet and red cell transfusions; Transfusion, 1993; 33:794–797.

H. Brandwein et al., Asahi Sepacell PL10A Leukocyte Removal Filter:Efficiency with Random Donor Platelet Pools, PALL Technical Report (undated).

J. Whitbread et al., Performance Evaluation of the Sepacell PL10A filter and Pall PXL 8 filter: measurement of Leukocyte Residuals and Consistency, PALL Technical Report (undated).

R. Brown et al., Evaluation of a new separation method utilizing plasma recirculation and autoelutriation, Transfusion, 1994; vol. 34, Supp.

Richard J. Sanderson et al., Design Principles for a Counterflow Centrifugation Cell Separation Chamber; Analytical Biochemistry 71, 615–622(1976).

Designed to Provide the Reliability and Performance to Harvest a High Yield Component Product, The Haemonetics V50 Apheresis System (undated).

Haemonetics Mobile Collection System Owner's Operating and Maintenance Manual, 1991 pp. 3–2 through 3–7 and pp. 1–6.

E.A. Burgstaler et al., White Blood Cell Contamination of Apheresis Platelets Collected on the COBE Spectra, COBE Blood Component Technology (undated).

T.H. Price et al., Platelet Collection Using the COBE Spectra, COBE Blood Component Technology (undated).

Nancy Besso et al., Asahi Sepacell PL–10A Leukocyte Removal Filter: Effect of Post–Filtration Flush WIth Saline, PALL Technical Report (undated).

Harvey J. Brandwein et al., Ashahi Sepacell PL–10A Leukocyte Removal Filter Description and Review of Claims, PALL Technical Report (undated).

"Lower is Better!", (flyer) PALL Biomedical Products Company (undated).

Judy H. Angelbeck, Adverse Reactions to Platelet Transfusion, Risks and Probable Causes (1994), pp. 1–14.

Centrifugal Elutriation, Beckman pp. 1–7, vi. (undated).

AS 104 Cell Separator, Fresenius (undated).

CS–3000 Blood Cell Separator, Powerful Technology, Fenwal Laboratories (undated).

Baxter CS–3000 Plus Blood Cell Separator Operator's Manual (7–19–3–136) (undated).

The Mobile Collection System gives you easier access to more donors than ever before, Haemonetics (Sep. 1992).

LRF6/LRF10, High Efficiency Leukocyte Removal Filter Systems For Platelets, PALL Biomedical Products Corporation (undated).

J. Whitbread et al., Reduction of C3A Fragment Levels Following Leukodepletion Using a PALL PXL8 Filter (undated).

T. A. Takahashi et al., Bradykinin Formation in a Platelet Concentrate Filtered with a Leukocyte–removal Filter Made of Nonwoven Polyester Fibers with a Negatively Charged Surface (undated).

Baxter CS–3000 Plus Blood Cell Separator pp. 1–18 (undated).

J.F. Jemionek, Variations in CCE Protocol for Cell Isolation, Elutriation, pp. 17–41 (undated).

Brief Operating Instructions, Fresenius MT AS 104 blood cell separator, 4/6.90(OP) (undated).

English language abstract of SU 1725117 A.

English language abstract of SU 1255136.

English language abstract of SU 1236366.

English language abstract of SU 1091071.

English language abstract of DE 3734170.

Multi Chamber Counterflow Centrifugation System, Dijkstra Vereenigde B.V., 13 pgs. (undated).

Baxter CS–3000 Plus Blood Cell Separator, Technology With a Mind You Can Own, 1990.

Aart Plas, Theo de Witte, Hans Wessels, and Clements Haanen, "A New Multi–chamber Counterflow Centrifugation Rotor with High–separation Capacity and Versatile Potentials," Experimental Hematology 16:355–359 (1988) International Society for Experimental Hematology.

Michael G. Kauffman, Stephen J. Noga, Thomas J. Kelly, and Albert D. Donnenberg, "Isolation of Cell Cycle Fractions by Counterflow Centrifugal Elutriation," Analytical Biochemistry 191, 41–46 (1990).

A. Faradji, A. Bohbot, M. Schmitt–Goguel, J.C. Siffert, S. Dumont, M.L. Wiesel, Y. Piemont, A.Eischen, J.P. Bergerat J. Bartholeyns, P. Poindron, J.P. Witz, F. Oberling, "Large Scale Isolation of Human Blood Monocytes by Continuous Flow Centrifugation Leukapherisis and Counterflow Centrifugation Elutriation for Adoptive Cellular Immunotherapy in Cancer Patients," Journal of Immunological Methods 174 (1994) 297–309.

Ino K. Gao, Stephn J. Noga, John E. Wagner, Carol A. Cremo, Janice Davis and Albert D. Donnenberg , "Implementation of a Semiclosed Large Scale Centrifugal Elutriation System," Journal of Clinical Apheresis 3:154–160 (1987).

Owen M. Griffith, "Separation of T and B Cells from Human Peripheral Blood by Centrifugal Elutriation," Analytical Biochemistry 87, 97–107 (1978).

Carl G. Figdor, Willy S. Bont, Ivo Touw, Johan de Roos, Eddy E. Roosnek and Jan E. de Vries, "Isolation of Functionally Different Human Monocytes by Counterflow Centrifugation Elutriation," Blood, vol. 60, No. 1, 46–52.

Jan Marc Orenstein, et al., "Microemboli Observed in Deaths Following Cardiopulmonary Bypass Surgery: Silicon Antifoam Agent and Polyvinyl Chloride Tubing as Sources of Emboli," Human Pathology, vol. 13, No. 12, (Dec. 1982), pp. 1082–1090.

I.R. Schmolka, "Polyalkylene Oxide Block Copolymers" Nonionic Surfactants, Chapt. 10, p. 300–371 (1967).

Lee, et al., "Protein–resistant surfaces prepared by PEO–containing block copolymer surfactants," Journal of Biomedical Materials Research, vol. 23, 351–368 (1989).

Mansoor Amiji et al., "Prevention of protein adsorption and platelet adhesion on surfaces by PEO/PPO/PEO triblock copolymers," Biomaterials 1992, vol. 13, No. 10, 682–692.

Hymes, et al. Pluronics: First Use as a Plasma Expander (Abstract) Abstracts of the 40th Scientific Sessions, Supplement to Circulation vols. XXXV and XXXVI, (Oct. 1967).

Yoshimasa Miyauchi, et al., "Adjunctive Use of a Surface–Active Agent in Extracorporeal Circulation," Supplement I to Circulation vols. XXXIII and XXXIV, Apr. 1966 pp. 171–177.

E.S. Wright, et al., "Fat globulemia in extracorporeal circulation," Surgery, vol. 53 No. 4, pp. 500–504, (Apr. 1963).

R. Champlin, "Purging: the separation of normal from malignant cells for autologous transplantation," Transfusion 1996, vol. 36, 910–918.

Jan Grimm, et al., "Separation and charaterization of mobilized and unmobilized peripheral blood progenitor cells by couonterflow centrifugal elutriation", Experimental Hematology 23: 535–544 (1995).

Herbein, et al., "Isolation and Identification of Two CD34+ Cell Subpopulations from Normal Human Peripheral Blood," Stem Cells 1994: 12:187–197.

L. Teofili, et al., "Separation of chemotherapy plus G–CS-F–mobilized peripheral blood mononuclear cells by counterflow centrifugal elutriation: in vitro characterization of two different CD34+ cell populations," Bone Marrow Transplantation (1996) 18, 421–425.

Keng, et al., "Characterization of the biophysical properties of human tumor and bone marrow cells as a preliminary step to the use of centrifugal elutriation in autologous bone marrow transplantation,"Radiation Oncology Biology Physics (Oct. 1984) vol. 10, No. 10, 1913–1922.

Lutz, et al., "Large–scale cell separation by centrifugal elutriation," Analytical Biochemistry 200, 376–380 (1992).

Orlic, et al., "Biological properties of subpopulations of pluripotent Hematopoietic stem cells enriched by elutriation and flow cytometry," Blood Cells (1994) 20: 107–120.

Hillyer, et al., "CD34+ progenitors and colony–forming units–granulocyte macrophage are recruited during large–volume leukapheresis and concentrated by counterflow centrifugal elutriation," Transfusion , vol. 33, No. 4, pp. 316–321 (1993).

Gengozian, et al., "Separation of feline bone marrow cells by counterflow centrifugal elutriation," Transplantation, vol. 60, 836–841, No. 8, Oct. 1995.

Nichol, et al., "Enrichment and Characterization of peripheral blood–derived megakarycocyte progenitors that mature in short–term liquid culture," Stem Cells 1994: 12: 494–505.

Ossevoort, et al., "A rapid isolation procedure for dendritic cells from mouse spleen by centrifugal elutriation," Journal of Immunological Methods 155 (1992) 101–111.

P.C. Keng, "High–Capacity Separation of Homogeneous Cell Subpopulations by Centrifugal Elutriation,"American Chemical Society, 103–112 (1991).

Pretlow II, et al., "Sedimentation of Cells: An Overview and Discussion of Artifacts," Cell Separation: Methods and Selected Applications, vol. 1, 41–60, (1982).

Wagner, et al., "Lymphocyte Depletion of Donor Bone Marrow by Counterflow Centrifugal Elutriation: Results of a Phase I Clinical Trial," Blood, 72, No. 4, (1988), 1168–1176.

De Witte, et al., "Cell Size Monitored Counterflow Centrifigation of Human Bone Marrow Resulting in Clonogenic Cell Fractions Substantially Depleted of Small Lymphocytes," Journal of Immunological Methods, 65 (1983) 171–182.

Noga, et al., "Using Elutriation to Engineer Bone Marrow Allografts, " Bone Marrow purging and Processing, 345–361, (1990).

Keng, et al., "Evaluation of Cell Subpopulations Isolated from Human Tumor Xenografts by Centrifugal Elutriation," Int. J. Radiation Oncology Biol. Phys. vol 18, pp. 1061–1067 (1990).

Monroy, et al., "Centrifugal Elutriation," Plasma Ther. Transfus. Technol. 1986, vol. 7: 389–394.

Uchida, et al., "Searching for hematopoietic stem cells II. The heterogeneity of Thy–1.1$^{lo}$Lin$^{–lo}$Sca–1+ mouse hematopoietic cells separated by counterflow centrifugal elutriation," Experimental Hematology 24:649–659 (1996).

Jones, et al., "Separation of Pluripotent Haematopoietic stem cells from spleen colony forming cells," Nature, vol. 347, 188–189 (1990).

Suzuki, et al., "Centrifugal elutriation and characterization of tumor cells from venoud blood of tumor–bearing mice: possible relevance to metastasis," Cancer Research 44, 3505–3511, (Aug. 1994).

Schattenberg, et al., "Allogeneic Bone Marrow Transplantatiton for Leukemia with Marrow Grafts Depleted of Lymphocytes by Counterflow Centrifugal," Blood, vol. 75, No. 6 (Mar. 1990), pp.1356–1363.

Van Es, et al., "An Improved Method for the Fractionation of Human Blood Cells by Centrifugal Elutriation," Analytical Biochemistry 103, 295–301, (1980).

Contreras, et al., "An Improved Technique for the Negative Selection of Large Numbers of Human Lymphocytes and Monocytes by Counterflow Centrifugation–Elutriation," Cellular Immunology 54, 215–229 (1980).

Stevenson, et al., "A System for Obtaining Large Numbers of Cryopreserved Human Monocytes Purified by Leukapheresis and Counter–current Centrifugation Elutriation (CCE)," Journal of Immunological Methods, 62 (1983), 353–363.

Jemionek, et al., "Fractionation of mammalian bone marrow by counterflow centrifugation–elutriation using a continuous albumin gradient:; analysis of granulocyte–macrophage colony–forming units," British Journal of Haematology, 1982, 50, 257–267.

De Witte, et al.., "Depletion of donor lymphocytes by counterflow centrifugation successfully prevents acute graft–versus–host disease in matched allogeneic marrow transplantation," Blood vol. 67, No. 5, (May 1986) 1302–1308.

Hemasure to Collaborate with American Red Cross on Tumor Cells Removal Technology, PR Newshire HemaSure Inc. Jan. 30, 1996.

Kolber, et al., "Target Cell Lysis by Cytototoxic T Lymphocytes redirected by Antibody–Coated Polystyrene Beads," The Journl of Immunology, vol. 143, 1461–1466, No. 5, Sep. 1989.

Blazar, et al. "Comparison of Three Techniques for the ex vivo Elimination of T Cells from Human Bone Marrow," Experimental hamatology, 13:123–128 (1985).

Quinones, et al., "Extended–Cycle Elutriation to Adjust T–Cell Content in HLA–Disparate Bone Marrow Transplantation," Blood vol. 82, No. 1, 307–318, (1993).

G.B. Nash, "Filterability of Blood Cells: Methods and Clinical Applications" Biorheology, 27: 873–882 (1990).

Linda A. Chambers, "Characteristics and Clinical Application of Blood Filters," Transfus Sci. 1989; 10: 207–218.

Lennie, et al., "Filterability of White Blood Cell Subpopulations, Separated by an Improved Method," Clinical Hemorheology, vol. 7, pp. 811–816, (1987).

Marcus, et al., "CFU–GM and T cell subsets in young red cell collections," Trans., vol.. 24, No. 5, pp. 379–381 (1984).

Bruisten, et al., "Efficiency of white cell filtration and a freeze–thaw procedure for removal of HIV–infected cells from blood," Transfusion vol. 30, pp. 833–837 (1990).

Nash, et al., "Methods and theory for analysis of flow of white cell sub–populations through micropore filters," British Journal of Haematology, 1988, 70: 165–170.

Ciuffetti, et al., "Human leucocyte rheology and tissue ischaemia," European Journal of Clinical Investigation (1989) 19, 323–327.

van Prooijen, et al., "Prevention of primary transfusion–assoicated cytomegalovirus infection in bone marrow transplant recipients by the removal of white cells from blood components with high–affinity filters," British Journal of Haematology (1994) 87, pp. 144–147.

Palathumpat, et al., "Different Subsets of T cells in the adult mouse bone marrow and spleen induce or suppres acute graft–versus–host disease," The Journal of Immunology, vol. 149, pp. 808–817 (1992).

Palathumpat, et al., "Studies of CD4–CD8–αβ Bone Marrow T Cells with Suppressor Activity," Journal of Immunology, vol. 148, pp. 373–380 (1992).

Schmidt–Wolf, et al., "T–cell subsets and suppressor cells in human bone marrow," Blood, vol. 80 No. 12, (1992) pp. 3242–3250.

Topolsky, et al., "Unrelated donor bone marrow transplantation without T cell depletion using a chemotherapy only conditioning regimen. Low incidence of failed engraftment and severs acuteGVHD," Bone Marrow Transplantation, vol. 17, 1996, pp. 549–554.

Palathumpat, et al., "A novel cell separation technique for the enrichment of committed and uncommited human hematopoietic progenitor cells and T cell depletion," Experimental Hematology Today (1995), pp. 1–7.

Strang, et al., "Density adjusted cell sorting (DACS), a novel cell separation method using high density microspheres in combination with customized density gradient solution to enrich or deplete specific cell sub–populations," Experimental Hematology Today (1995) pp. 1–6.

Shpall, et al., "Bone Marrow Metastases," Hematology/Oncology Clinics of America, vol. 10 No. 2, (1996) pp. 321–343.

Trickett, et al., "Tumour cell purging for autologous bone marrow transplantation," Medical Laboratory Sciences, vol. 47, (1990) pp.120–131.

Gribben, et al., "Immunologic purging of marrow assessed by PCR before autologous bone marrow transplantation for B–cell lymphoma," The New England Journal of Medicine, vol. 325, No. 22, 1525–1532 (1991).

Jansen, et al., "Immunologic purging CD4+ and CD8+ cell depletion for patients at high risk for severe acute GVHD," Bone Marrow Transplantation (1996) vol. 17, pp. 377–382.

Quinones, et al., "Inhibition of Cytotoxic T cell lysis by anti–CD8 monoclonal antibodies: studies wiwth CD3–targeted cytolysis of nominal antigen–negative targets," The Journal of Immunology vol. 142, pp. 220–2206.

Lucas, et al., "Alternate donor sources in HLA–mismatched marrow transplantation: T cell depletion of surgically cadaveric marrow," Marrow Transplanation (1988) 3, 211–220.

Lunsted, et al., "The Synthesis and Properties of block cocpolymer polyol surfactants," pp. 1–111.

METHODS FOR SEPARATION OF PARTICLES

BACKGROUND OF THE INVENTION

1. Field of the Invention

The present invention relates to a system and method for separating particles. The invention has particular advantages in connection with separating tumor cells from blood components, such as red blood cells and/or stem cells.

This application is related to U.S. Pat. No. 5,674,173, issued on Oct. 7, 1997; U.S. patent application Ser. No. 08/423,583, filed on Apr. 18, 1995 (abandoned); and U.S. patent application Ser. No. 08/634,167, filed on Apr. 18, 1996, U.S. Pat. No. 5,939,319. The entire disclosure of this U.S. patent and the entire disclosures of these U.S. patent applications are incorporated herein by reference.

2. Description of the Related Art

In many different fields, liquids carrying particle substances must be filtered or processed to obtain either a purified liquid or purified particle end product. In its broadest sense, a filter is any device capable of removing or separating particles from a substance. Thus, the term "filter" as used herein is not limited to a porous media material but includes many different types of processes where particles are either separated from one another or from liquid.

In the medical field, it is often necessary to filter blood. Whole blood consists of various liquid components and particle components. Sometimes, the particle components are referred to as "formed elements". The liquid portion of blood is largely made up of plasma, and the particle components primarily include red blood cells (erythrocytes), white blood cells (including leukocytes), and platelets (thrombocytes). While these constituents have similar densities, their average density relationship, in order of decreasing density, is as follows: red blood cells, white blood cells, platelets, and plasma. In addition, the particle constituents are related according to size, in order of decreasing size, as follows: white blood cells, red blood cells, and platelets.

In addition to red and white blood cells (and their subsets such as T cells and stem cells), plasma, and platelets, blood also includes in some cases, tumor cells. These cells have substantially similar densities, but different sedimentation velocities. Generally, stem cells have a sedimentation velocity greater than that of T cells and less than that of tumor cells.

Most current purification devices rely on density and size differences or surface chemistry characteristics to separate and/or filter blood components for transfusion or reinfusion purposes. Typically, blood components are separated or harvested from other blood components using a centrifuge. The centrifuge rotates a blood reservoir to separate components within the reservoir using centrifugal force. In use, blood enters the reservoir while it is rotating at a very rapid speed and centrifugal force stratifies the blood components, so that particular components may be separately removed. Although some centrifugal separation techniques are effective at separating some blood components from one another, many centrifugal separation processes are not capable of producing a highly purified end product.

In one type of separation procedure, a peripheral blood collection (withdrawn from an artery or vein) or a bone marrow blood collection is purified in a centrifugal separation process to isolate what is known as a peripheral cell collection or bone marrow cell collection, respectively. The peripheral cell collection or bone marrow cell collection primarily includes plasma, red blood cells, stem cells, and T cells, and may also include tumor cells if the donor's blood included such cells.

After undergoing a therapeutic treatment, such as chemotherapy or radiation therapy, to eliminate cancerous tumor cells, cancer patients often receive a transfusion of a peripheral cell collection or a bone marrow cell collection to replace stem cells destroyed as a side effect of the treatment. To reduce risks associated with infusing blood components from a foreign donor, some of these transfusions are autologous, where blood components collected from the patient are later reinfused back to the patient. However, the blood components initially collected from cancer patients may include cancerous tumor cells, which are then infused back into the cancer patient during reinfusion. This reinfusion of tumor cells may diminish the effectiveness of therapeutic treatments aimed at reducing cancerous tumor cells in a patient's body. Removal of tumor cells from a peripheral cell collection or bone marrow cell collection before transfusion, however, is extremely difficult.

Prior attempts to separate stem cells from tumor cells prior to reinfusion have had limited success. In one separation method, a selective antibody is introduced into a collected blood component sample after separating a substantial number of platelets and red blood cells from the sample. The selective antibody chemically attaches to stem cells to "mark" them. To separate the marked stem cells from the remaining blood components, the collected blood components are passed between stationary beads coated with a material which chemically bonds with the selective antibody. These chemical bonds retain the marked stem cells on the beads to filter them from the remaining blood components.

To remove the marked stem cells from the beads, an operator agitates the beads or flushes a chemical solution through the beads to break the chemical bonds between the material and selective antibody. This separation process, however, is extremely expensive, tedious, and time consuming. In addition, the beads do not remove a significant number of stem cells, and a substantial number of tumor cells often remain in the separated end product.

In another type of separation procedure, magnetic particles or fluid having an attached antibody are added to a blood component collection. The antibody chemically binds with stem cells in the sample to link the magnetic particles and stem cells together. To separate the stem cells, a magnetic separator is used to attract the linked magnetic substance and stem cells, and a substance is then added to break the chemical bonds between the stem cells and magnetic substance.

Although this separation procedure is capable of separating some stem cells and tumor cells, it is expensive and labor intensive. A significant number of tumor cells remain in the separated end product and a sizable number of stem cells are not recovered. In addition, the substances added to the blood sample in both the bead separation process and the magnetic separation process are potentially toxic if they are infused along with the separated blood components.

Centrifugal elutriation is another process used to separate tumor cells from stem cells. This process separates cells suspended in a liquid medium without the use of chemical antibodies. In one common form of elutriation, a cell batch is introduced into a flow of liquid elutriation buffer. This liquid which carries the cell batch in suspension, is then introduced into a funnel-shaped chamber located in a spinning centrifuge. As additional liquid buffer solution flows through the chamber, the liquid sweeps smaller sized, slower-sedimenting cells toward an elutriation boundary within the chamber, while larger, faster-sedimenting cells migrate to an area of the chamber having the greatest centrifugal force.

When the centrifugal force and force generated by the fluid flow are balanced, the fluid flow is increased to force slower-sedimenting cells from an exit port in the chamber, while faster-sedimenting cells are retained in the chamber. If fluid flow through the chamber is increased, progressively larger, faster-sedimenting cells may be removed from the chamber.

Thus, centrifugal elutriation separates particles having different sedimentation velocities. Stoke's law describes sedimentation velocity (SV) of a spherical particle, as follows:

$$SV = \frac{2}{9} \frac{r^2 (\rho_p - \rho_m) g}{\eta}$$

where, r is the radius of the particle, $\rho_p$ is the density of the particle, $\rho_m$ is the density of the liquid medium, $\eta$ is the viscosity of the medium, and g is the gravitational or centrifugal acceleration. Because the radius of a particle is raised to the second power in the Stoke's equation and the density of the particle is not, the size of a cell, rather than its density, greatly influences its sedimentation rate. This explains why larger particles generally remain in a chamber during centrifugal elutriation, while smaller particles are released, if the particles have similar densities.

As described in U.S. Pat. No. 3,825,175 to Sartory, centrifugal elutriation has a number of limitations. In most of these processes, particles must be introduced within a flow of fluid medium in separate discontinuous batches to allow for sufficient particle separation. Thus, some elutriation processes only permit separation in particle batches and require an additional fluid medium to transport particles. In addition, flow forces must be precisely balanced against centrifugal force to allow for proper particle segregation.

Further, a Coriolis jetting effect takes place when liquid and particles flow into an elutriation chamber from a high centrifugal field toward a lower centrifugal field. The liquid and particles turbulently collide with an inner wall of the chamber facing the rotational direction of the centrifuge. This phenomenon mixes particles within the chamber and reduces the effectiveness of the separation process. Coriolis jetting also shunts flow of liquid and particles along the inner wall of the elutriation chamber from the inlet directly to the outlet. Thus, particles pass around the elutriative field to contaminate the end product.

If the combined density of particles and liquid in the elutriation chamber is significantly greater than the density of liquid entering the chamber, Coriolis jetting increases. This is because the relatively low density liquid entering the elutriation chamber encounters increased buoyant forces tending to accelerate the flow of liquid toward the outlet of the elutriation chamber. When the accelerated flow of liquid encounters tangential forces in the chamber, the flow of liquid may form a Coriolis jet capable of carrying larger, relatively faster sedimenting particles, such as tumor cells, around the elutriative field and through an outlet of the chamber.

Particle mixing by particle density inversion is an additional problem encountered in some prior elutriation processes. Fluid flowing within the elutriation chamber has a decreasing velocity as it flows in the centripetal direction from an entrance port toward an increased cross-sectional portion of the chamber. Because particles tend to concentrate within a flowing liquid in areas of lower flow velocity, rather than in areas of high flow velocity, the particles concentrate near the increased cross-sectional area of the chamber. Correspondingly, since flow velocity is greatest adjacent the entrance port, the particle concentration is reduced in this area. Density inversion of particles takes place when the centrifugal force urges the particles from the high particle concentration at the portion of increased cross-section toward the entrance port. This particle turnover reduces the effectiveness of particle separation by elutriation.

Particle adhesion is another problem associated with elutriation and other types of particle separation processes. Two types of particle adhesion reduce the effectiveness of particle separation. In the first type of particle adhesion, individual particles are bound to one another so that they act as groups of particles. When a substance including these particle groups is separated in a elutriative process or other separation process in which particle size is a factor, each group of particles acts as a larger particle and becomes separated along with larger particles, rather than being separated into smaller individual particles. In the second type of particle adhesion, particles adhere to equipment used during a separation procedure, such as plastic tubing or an elutriation chamber. This lowers the overall yield of particles, in particular, when separating a small number of particles.

For these and other reasons, there is a need to improve particle separation.

SUMMARY OF THE INVENTION

Accordingly, the present invention is directed to a method and system that substantially obviates one or more of the limitations of the related art. To achieve these and other advantages and in accordance with the purpose of the invention, as embodied and broadly described herein, the invention includes a method of separating first particles and second particles having different sedimentation velocities. In the method, a fluid chamber is rotated about an axis of rotation and a first liquid carrying the first and second particles is passed into the fluid chamber. A saturated fluidized bed including the first particles is formed in the fluid chamber. The saturated fluidized bed retains the second particles in the fluid chamber. The method also includes flowing into the fluid chamber a second liquid, the second liquid having a density less than that of the first and second particles so that the second liquid reduces overall density of substances in the fluid chamber and thereby reduces Coriolis jetting of at least one of the first and second liquid in the fluid chamber. The first liquid, the second liquid, and at least a portion of the first particles are allowed to flow from the fluid chamber.

In another aspect, the invention includes a method of separating tumor cells from a cell suspension. The method includes flowing a cell suspension including at least a first liquid, first cells, and tumor cells into the fluid chamber. A second liquid and the first liquid are mixed. The second liquid has a density less than that of the cell suspension so that the second liquid reduces overall density of substances in the fluid chamber and thereby limits Coriolis jetting of at least one of the first liquid and the second liquid in the fluid chamber. A saturated fluidized bed including at least the first cells is formed in the fluid chamber. The saturated fluidized bed retains tumor cells in the fluid chamber, and at least the first liquid, the second liquid, and at least a portion of the first cells are allowed to flow from the fluid chamber.

In a further aspect, the present invention includes a method of reducing particle adhesion in a particle separation procedure. The method includes flowing liquid carrying particles into a fluid chamber and separating the particles in the fluid chamber according to differences in sedimentation velocity. A polymer is added to the liquid; the polymer has the chemical formula HO—$(CH_2CH_2O)_A$—$(CHCH_3CH_2O)_B$—$(CH_2CH_2O)_A$—H, wherein A satisfies the expression $0 \leq A \leq 150$ and B satisfies the expression $0 \leq B \leq 100$. The polymer reduces adherence of at least some of the particles to improve separation of the particles.

In yet another aspect, the present invention includes a system for use in separating particles. A fluid chamber is provided for separating particles. The fluid chamber includes a first section having an inlet allowing flow of liquid carrying particles into the fluid chamber, and a second section having an outlet allowing flow of liquid and particles from the fluid chamber after separation of at least some of the particles in the fluid chamber, the first and second sections forming an interior having a maximum cross-sectional area at a position intermediate the inlet and outlet, the interior converging from the position of the maximum cross-sectional area toward the inlet. An inlet line is coupled to the inlet of the fluid chamber. The inlet line is configured for flow-connection to a source containing the liquid carrying particles. At least one of the fluid chamber and the inlet line includes the above-mentioned polymer.

In a further aspect, a separation vessel having a collection well for retaining particles therein is provided. The separation vessel includes an inlet, a particle concentrate outlet for removing at least the particles from the collection well, and a liquid outlet for removing at least the liquids from the separation vessel, the inlet of the separation vessel being flow connected to the outlet of the fluid chamber.

It is to be understood that both the foregoing general description and the following detailed description are exemplary, and are intended to provide further explanation of the invention as claimed.

BRIEF DESCRIPTION OF THE DRAWINGS

The accompanying drawings are included to provide a further understanding of the invention and are incorporated in and constitute a part of this specification. The drawings illustrate an embodiment of the invention and, together with the description, serve to explain the principles of the invention. In the drawings.

DESCRIPTION OF THE PREFERRED EMBODIMENT

Reference will now be made in detail to the present preferred embodiment of the invention, an example of which is illustrated in the accompanying drawings. Wherever possible, the same reference numbers are used in the drawings and the description to refer to the same or like parts.

The embodiment of the present invention preferably includes a COBE® SPECTRA™ blood component centrifuge manufactured by Cobe Laboratories of Colorado. The COBE® SPECTRA™ centrifuge incorporates a one-omega/two-omega sealless tubing connection as disclosed in U.S. Pat. No. 4,425,112 to Ito, the entire disclosure of which is incorporated herein by reference. Although the embodiment of the invention is described in combination with the COBE® SPECTRA™ centrifuge, this reference is made for exemplary purposes only and is not intended to limit the invention in any sense.

As will be apparent to one having skill in the art, the present invention may be advantageously used in a variety of centrifuge devices commonly used to separate blood into its components. In particular, the present invention may be used with any centrifugal apparatus regardless of whether or not the apparatus employs a one-omega/two-omega sealless tubing connection.

Figure 1:
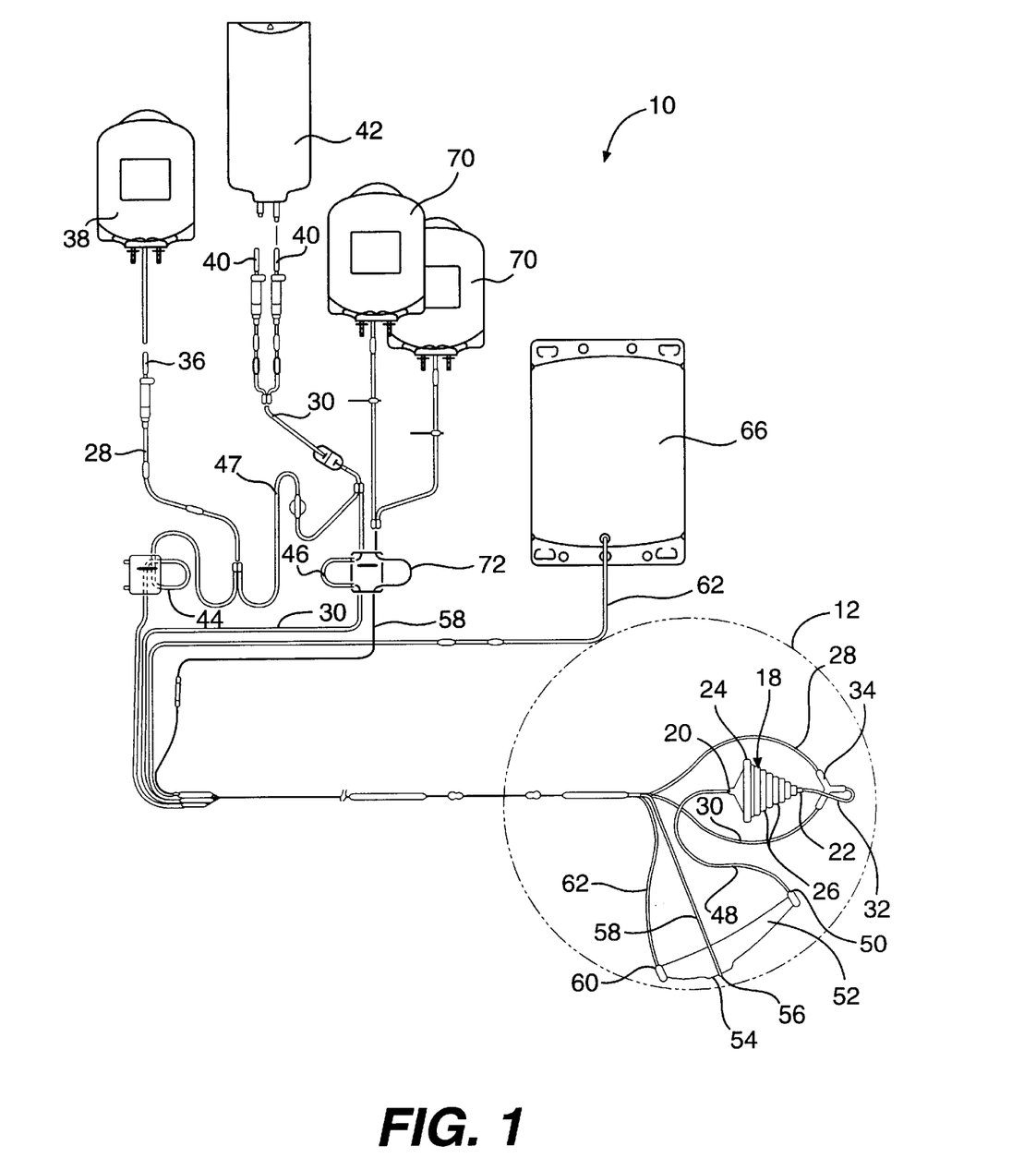
FIG. 1 is a schematic diagram of a particle separation system in accordance with an embodiment of the invention.

As embodied herein and illustrated in FIG. 1, the present invention includes a particle separation system 10 having a centrifuge rotor 12. Preferably, the centrifuge rotor 12 is coupled to a motor (not shown) via an arm 14, shown in FIG. 2, so that the centrifuge rotor 12 rotates about its axis of rotation A—A.

Figure 2:
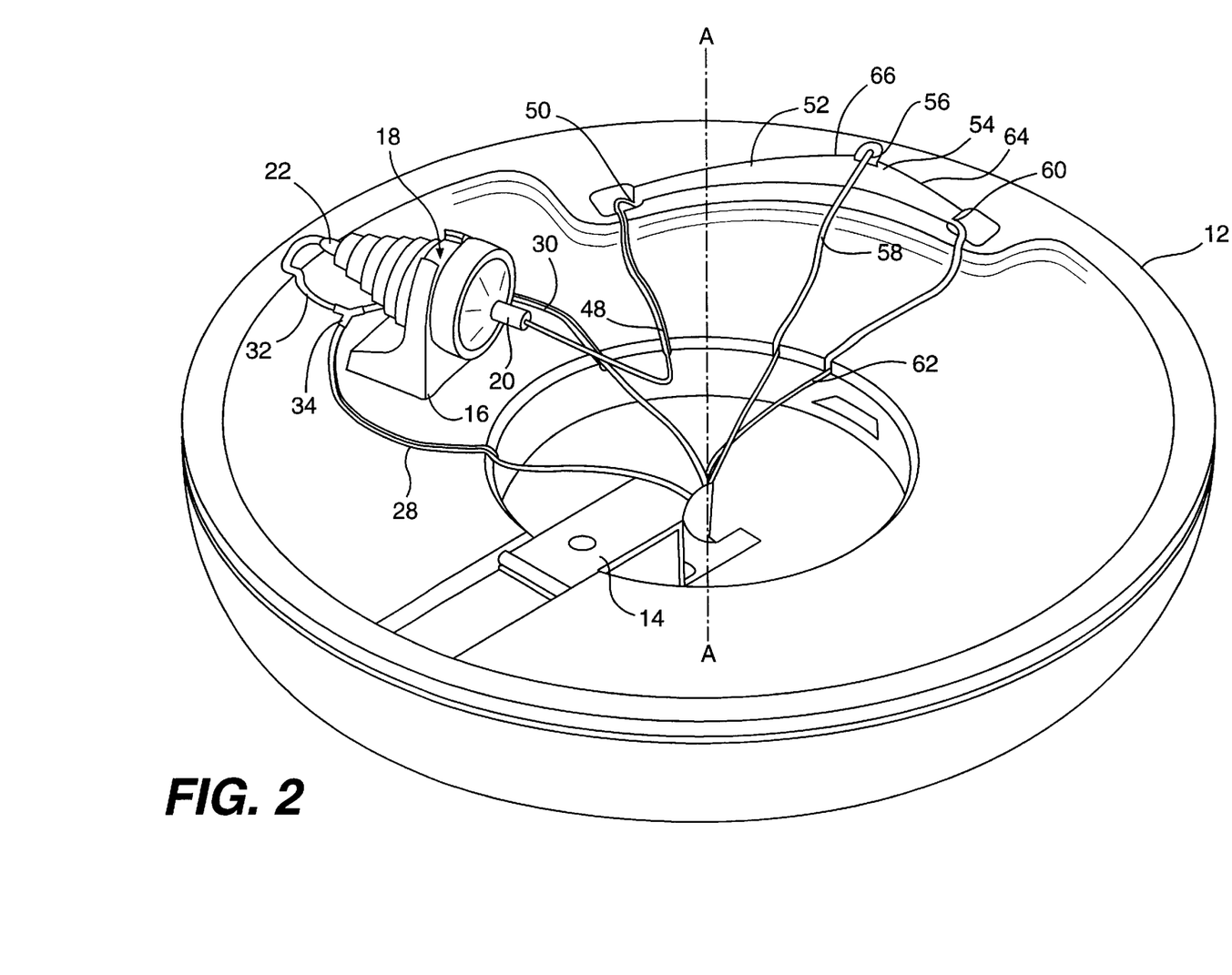
FIG. 2 is a perspective view of a fluid chamber and separation vessel mounted on a centrifuge rotor as depicted in FIG. 1.

As shown in FIG. 2, a holder 16 is provided on a top surface of the rotor 12. The holder 16 releasably holds a fluid chamber 18 on the rotor 12 such that an outlet 20 of the fluid chamber 18 is positioned closer to the axis of rotation A—A than an inlet 22 of the fluid chamber 18. The holder 16 preferably orients the fluid chamber 18 on the rotor 12 with a longitudinal axis of the fluid chamber 18 in a plane transverse to the rotor's axis of rotation A—A. In addition, the holder 16 is preferably arranged to hold the fluid chamber 18 on the rotor 12 with the fluid chamber outlet 20 facing the axis of rotation A—A. Although the holder 16 retains the fluid chamber 18 on a top surface of the rotor 12, the fluid chamber 18 may also be secured to the rotor 12 at alternate locations, such as beneath the top surface of the rotor 12.

The fluid chamber 18 is preferably constructed similar or identical to one of the fluid chambers disclosed in above-mentioned U.S. Pat. No. 5,674,173 and U.S. patent application Ser. No. 08/423,583, abandoned. As shown in FIGS. 1 and 2, the inlet 22 and outlet 20 of the fluid chamber 18 are arranged along a longitudinal axis of the fluid chamber 18. A wall of the fluid chamber 18 extends between the inlet 22 and outlet 20 thereby defining inlet 22, the outlet 20, and an interior of the fluid chamber 18.

The fluid chamber 18 includes two frustoconical shaped sections joined together at a maximum cross-sectional area of the fluid chamber 18. The interior of the fluid chamber 18 tapers (decreases in cross-section) from the maximum cross-sectional area in opposite directions toward the inlet 22 and the outlet 20. Although the fluid chamber 18 is depicted with two sections having frustoconical interior shapes, the interior of each section may be paraboloidal, or of any other shape having a major cross-sectional area greater than the inlet or outlet area.

The volume of the fluid chamber 18 should be at least large enough to accommodate the formation of a saturated fluidized particle bed (described below) for a particular range of flow rates, particle sizes, and rotational speeds of the centrifuge rotor 12. The fluid chamber 18 may be constructed from a unitary piece of plastic or from separate pieces joined together to form separate sections of the fluid chamber 18. The fluid chamber 18 may be formed of a transparent or translucent copolyester plastic, such as PETG, to allow viewing of the contents within the chamber interior with the aid of an optional strobe (not shown) during a separation procedure.

As shown in FIG. 1, a groove 24 is formed on an inner surface of the fluid chamber 18 at a position of the maximum cross-sectional area. The groove 24 is defined by top and bottom wall surfaces oriented substantially perpendicular to the longitudinal axis of the fluid chamber 18 and an inner surface of the fluid chamber 18 facing the longitudinal axis. Preferably, the groove 24 is annular, however, the groove 24 may also partially surround the longitudinal axis of the fluid chamber 18.

The groove 24 helps to disperse Coriolis jetting within the fluid chamber 18. Sudden increases in liquid flow rate during a particle separation procedure may limit the ability of the saturated fluidized particle bed to obstruct particle passage. Liquid flowing into the fluid chamber 18 may undergo a Coriolis jetting effect. This jetting flow reduces the filtration effectiveness of a saturated fluidized particle bed formed in the fluid chamber 18 because liquid and particles may pass between the saturated fluidized particle bed and an interior wall surface of the fluid chamber 18 rather than into the bed itself. The fluid chamber 18 including groove 24 counteracts these effects by channeling Coriolis jetting flow in a circumferential direction partially around the axis of fluid chamber 18. Therefore, the groove 24 improves the particle obstruction capability of the saturated bed, especially when liquid flow rates increase.

A plurality of steps 26 are preferably formed on an inner surface of the fluid chamber 18 between the maximum cross-section of the chamber 18 and the inlet 22. Each step 26 has a base surface oriented substantially perpendicular to the longitudinal axis of the fluid chamber 18, as well as a side surface positioned orthogonal to the base surface. Although FIG. 1 depicts a corner where the side surface and the base surface intersect, a concave groove may replace this corner. In a preferred embodiment, each step 26 is annular and surrounds the axis of the chamber 18 completely to bound a cylindrical shaped area. Alternatively, the steps 26 may partially surround the axis of the chamber 18.

The inclusion of steps 26 in the fluid chamber 18, also improves the particle obstruction characteristics of a saturated fluidized particle bed formed in the fluid chamber 18, in particular during increases in the rate of fluid flow. The steps 26 provide this improvement by providing momentum deflecting and redirecting surfaces to reduce Coriolis jetting in fluid chamber 18. When Coriolis jetting takes place, the liquid and particles of the jet travel along an interior surface of the fluid chamber 18 that faces the direction of centrifuge rotation. Therefore, the jet may transport particles between the fluid chamber interior surface and either a saturated fluidized particle bed or an elutriation field positioned in the fluid chamber 18. Thus, particles traveling in the jet may exit the fluid chamber 18 without being separated.

Steps 26 direct or alter the momentum of the Coriolis jet flow of liquid and particles generally in a circumferential direction about the axis of the fluid chamber 18. Thus, a substantial number of particles originally flowing in the jet must enter the saturated fluidized bed or elutriation field to be separated.

The groove 24 and steps 26 are provided to facilitate fluid flow rate increases, as well as to improve steady state performance of the fluid chamber 18. During blood component separation, the groove 24 and steps 26 greatly reduce the number of filtered cells, such as tumor cells, that would otherwise bypass a saturated fluidized particle bed formed in the fluid chamber 18.

As shown in FIG. 1, the system 10 further includes a first conduit 28, second conduit 30, an inlet line 32 in fluid communication with the inlet 22 of the fluid chamber 18, and a three-way connector 34 having three legs for flow-connecting the first conduit 28, second conduit 30, and inlet line 32. The first conduit 28 includes a coupling 36 for flow-connecting the first conduit 28 with a first source 38 containing liquid carrying particles to be separated from one another. Likewise, the second conduit 30 includes couplings 40 for flow-connecting the second conduit 30 with a second source 42 containing a diluting liquid. The couplings 36 and 40 are preferably any type of common medical coupling devices, such as spikes or sterile tubing connectors.

As shown in FIG. 1, the first conduit 28 includes a first tubing loop 44, and the second conduit 30 includes a second tubing loop 46. During use, the first and second tubing loops 44 and 46 are mounted in peristaltic pumps (not shown) for respectively pumping the fluid to be separated and the diluting liquid from the first and second sources 38 and 42, respectively.

A line 47 is provided to continue the flow of diluting liquid into the first conduit 28 after the first source 38 and upper part of first conduit 28 are empty. Fluid communication of the upper part of first conduit 28 and the line 47 with the lower part of first conduit 28 is preferably controlled by pinch valves (not shown). The continued flow of diluting liquid into first conduit 28 allows flushing of any remaining particles in first conduit 28 into the fluid chamber 18, and allows the continued perfusion of the fluid chamber 18 with diluting liquid to continue the separation process in the fluid chamber 18.

Preferably, the density of the diluting liquid in the second source 42 is less than the density of both the particles and liquid in the first source 38. As described below, the fluid to be separated and diluting liquid mix with one another in the three-way connector 34 and the diluting liquid regulates (lowers) the overall density of substances flowing in the fluid chamber 18.

Preferably, the liquid and particles in the first source 38 are a cell suspension including blood components, such as a peripheral cell collection or bone marrow cell collection primarily including plasma, red blood cells, stem cells, and T cells. If the original donor's blood included tumor cells, the cell collection in the first source 38 would also include tumor cells.

In a preferred embodiment, the diluting liquid in the second source 40 is a solution including electrolytes. To ensure that the diluting solution is not detrimental to the blood components, the electrolyte solution has a pH of preferably from about 5.0 to about 8.0, more preferably from about 7.0 to about 7.8, and most preferably about 7.4. For example, the electrolyte solution is a conventional saline solution, lactated ringers solution, or dextrose saline solution having a pH of about 7.4.

Preferably, the diluting liquid is a substance known a ISOLYTE® S pH 7.4 (Multi-Electrolyte Injection) manufactured by McGaw, Inc. This substance has the following amounts of electrolyte in units of mEq/liter:

| | | | | | |
|---|---|---|---|---|---|
| $Na^+$ | 141 | $Mg^+$ | 3 | Phosphate | 1 |
| $K^+$ | 5 | $Cl^-$ | 98 | $(HPO_4)$ | |
| | | Acetate | 27 | (0.5 mmole P/L) | |
| | | | | Gluconate | 23 |

Each 100 mL of ISOLYTE® contains Sodium Chloride USP 0.53 g, Sodium Gluconate USP 0.5 g, Sodium Acetate.$3H_2O$ USP 0.37 g, Potassium Chloride USP 0.037 g, Magnesium Chloride.$6H_2O$ USP 0.03 g, Dibasic Sodium Phosphate.$7H_2O$ USP 0.012 g, Monobasic Potassium Phosphate NF 0.00082g, and Water for Injection USP qs. In addition, this substance may also include Glacial Acetic Acid USP or Sodium Hydroxide NF to adjust pH so that the pH is about 7.4. ISOLYTE® has a calculated Osmolarity of 295 mOsmo/liter, a density of 1.005 gm/ml at 25 degrees Celsius, and a viscosity of 1.02 cp at 22 degrees Celsius.

Optionally, liquid and particles in the first source 38 and/or the diluting liquid in the second source 40 include up to about 2% by weight of a polymer material for reducing adherence of the particles to one another and for reducing adherence of the particles to components of the system 10. For example, this polymer material is a triblock, polyethylene oxide—polypropylene oxide—polyethylene oxide copolymer having the chemical formula $HO-(CH_2CH_2O)_A-(CHCH_3CH_2O)_B-(CH_2CH_2O)_A-H$, wherein A satisfies the expression $0 \leq A \leq 150$ and B satisfies the expression $0 \leq B \leq 100$. In a preferred embodiment, A is 75 or 76 and B is 30. For example, the polymer material is preferably PLURONIC® F68 or PLURACARE® F68 Prill manufactured by BASF Corp. As described below, the use of these polymer materials improves particle separation in the fluid chamber 18 and increases the yield of separated particles, in particular, when the separated particles are small in number.

The liquid and particles from the first source 38 and the diluting liquid from the second source 40 flow through the respective first conduit 28 and second conduit 30 to the three-way connector 34. These substances mix in the three-way connector 34 and flow through the inlet line 32 into the fluid chamber 18. In the fluid chamber 18, turning with rotor 12, the particles separate according to differences in sedimentation velocity leaving faster sedimenting particles in the fluid chamber 18 and allowing slower sedimenting particles to flow from the fluid chamber 18, as described below.

After the particles are separated in the fluid chamber 18, the liquid and particles having a relatively slower sedimentation velocity flow through the fluid chamber outlet 20 into tubing 48. As shown in FIGS. 1 and 2, the tubing 48 is connected to an inlet 50 of a separation vessel 52 mounted to the centrifuge rotor 12. As described below, the separation vessel 52 separates particles from liquid.

Adjacent to an outer portion of the centrifuge rotor 12, the separation vessel 52 has a collection well 54 for collecting particles flowing into the separation vessel 52. Rotation of centrifuge rotor 12 sediments particles into the collection well 54 while slower sedimenting liquid and possibly some slower sedimenting particles remain above a top boundary of the collection well 54.

The collection well 54 has a particle concentrate outlet 56 connected to a particle concentrate line 58. The particle concentrate line 58 removes particles retained in the collection well 54 along with a small portion of liquid. The separation vessel 52 also includes a liquid outlet 60 connected to a liquid outlet line 62. The liquid outlet line 62 removes liquid flowing above a top boundary of the collection well 54. In addition, the liquid outlet line 62 may remove some slower sedimenting particles flowing past the collection well 54.

Preferably, liquid outlet 60 is located at or adjacent to one end of the separation vessel 52, and the inlet 50 is located at or adjacent to an opposite end of the separation vessel 52. This spacing ensures ample time for separation of particles from liquid, collection of a substantial number of particles in the collection well 54, and corresponding removal of a substantial number of particles through the particle concentrate line 58.

In the preferred embodiment shown in FIG. 2, the separation vessel 52 is placed in a groove 64 formed in the rotor 12. Preferably, the separation vessel 52 is a channel formed of a semi-rigid material so that a valley 66 in an outer wall of the groove 64 forms the collection well 54 when the separation vessel 52 expands in response to liquid and particles in the separation vessel 52 encountering centrifugal forces. As shown in FIG. 2, the top surface of the rotor 12 preferably includes retainer grooves for receiving the first and second conduits 28 and 30, three-way connector 34, inlet line 32, tubing 48, particle concentrate line 58, and liquid outlet line 62.

As shown in FIG. 1, the liquid outlet line 62 is fluidly coupled to a liquid collection container 66 for collecting liquid removed from the separation vessel 52, and the particle concentrate line 58 is fluidly coupled to one or more particle collection containers 70 for collecting particles removed from the separation vessel 52. Preferably, the particle concentrate line 58 includes a tubing loop 72 capable of being mounted in a peristaltic pump for pumping particles through the particle concentrate line 58. The pump for tubing loop 72 regulates the flow rate and concentration of particles in particle concentrate line 58. To control flow rates of substances and rotational speed of the rotor 12 during operation of the system 10, a controller (not shown) controls pumps (not shown) for pumping substances through the first conduit 28, second conduit 30, and particle concentrate line 58, and controls a motor (not shown) for rotating the centrifuge rotor 12.

Alternatively, components of the system 10, such as the first conduit 28, second conduit 30, inflow line 32, fluid chamber 18, tubing 48, separation vessel 52 and particle concentrate line 58, are formed at least partially with a polymer material for reducing adherence of the particles to components of the system 10. For example, this polymer material may include the triblock, polyethylene oxide—polypropylene oxide—polyethylene oxide copolymer, described above, having the chemical formula $HO-(CH_2CH_2O)_A-(CHCH_3CH_2O)_B-(CH_2CH_2O)_A-H$, wherein A satisfies the expression $0 \leq A \leq 150$ and B satisfies the expression $0 \leq B \leq 100$. In a preferred embodiment, A is 75 or 76 and B is 30. For example, the polymer material is preferably PLURONIC® F68 or PLURACARE® F68 Prill manufactured by BASF Corp. The use of these polymer materials for components of the system 10 improves particle separation in the fluid chamber 18 and increases the yield of separated particles, especially when the separated particles are small in number.

A preferred method of separating components of blood and separating tumor cells from a cell suspension is discussed below with reference to FIGS. 1–3. Although the invention is described in connection with a blood component separation process and a tumor cell separation process, it should be understood that the invention in its broadest sense is not so limited. The invention may be used to separate a number of different types of particles.

Initially, peripheral blood or bone marrow blood is collected from a patient and this blood is purified in a centrifugal separation process to isolate what is known as a peripheral cell collection or bone marrow cell collection, respectively. During this initial centrifugation process, platelet rich plasma and a portion of the red blood cells and more dense white blood cells are separated from the blood to obtain a peripheral cell collection or bone marrow cell collection primarily including plasma, red blood cells, stem cells, and T cells. In addition, this collection most likely includes some platelets and tumor cells, if the donor's blood included such cells. As described in more detail below and shown in FIG. 3, particular particles, such as red blood cells "R" and possibly some T cells "T", are used to form a saturated fluidized particle bed in the fluid chamber 18. If the number of red blood cells "R" in the peripheral cell collection is insufficient to form the saturated bed, additional red blood cells are preferably added to the first source 38 so that the number of red blood cells exceeds the number of stem cells, T cells, and any tumor cells in the first source 38.

The initial separation of the peripheral blood or bone marrow is preferably performed on a centrifuge (not shown) separate from the system 10, such as a dual stage or single stage centrifugal separator. In an alternative embodiment, the centrifuge rotor 12 may include structure for providing initial blood component separation on the centrifuge rotor 12, as disclosed in above-referenced U.S. Pat. No. 5,674,173 and U.S. patent application Ser. No. 08/423,583, abandoned.

The separated peripheral cell collection or bone marrow cell collection is placed in the first source 38 shown in FIG. 1, and the first source 38 is coupled to the first conduit 28. In addition, the second source 42 containing the diluting liquid is coupled to the second conduit 30. The centrifuge rotor 12 is rotated about the axis of rotation A—A, and the blood components and diluting liquid are pumped from the first and second sources 38 and 42 and through the first and second conduits 28 and 30, respectively.

For example, the centrifuge rotor 12 is rotated at a speed of about 2,400 RPM to generate about 776 g at the fluid chamber inlet 20 and about 466 g at the fluid chamber outlet 22. If possible, the highest feasible rotational speed of rotor 12 is used to maximize the dynamic range of flow rates used in the process. The equilibrium flow rates are related to the square of the rotational speed.

As the blood components and diluting liquid flow into the three-way connector 34, they mix with one another and flow into the fluid chamber 18 via the inlet line 32. Although the blood components and the diluting liquid are preferably mixed in the three-way connector 34 during the separation procedure, the substances could be mixed in different ways. For example, the diluting liquid could be added to the first source 38 to mix the diluting liquid and blood components in the first source 38. This mixture could also be performed before, or at the beginning of, a separation procedure.

Rotation of the centrifuge rotor 12 and the flow rate of substances entering the fluid chamber 18 are controlled to accumulate particles in the fluid chamber 18, while liquids, such as the plasma and diluting liquid flow from the fluid chamber 18. As shown schematically in FIG. 3, a fluidized particle bed, including red blood cells "R" and possibly some T cells "T," eventually forms in the largest cross-sectional portion of the fluid chamber 18. When more red blood cells "R" and T cells "T" flow into the particle bed, it reaches a state of saturation.

Figure 3:
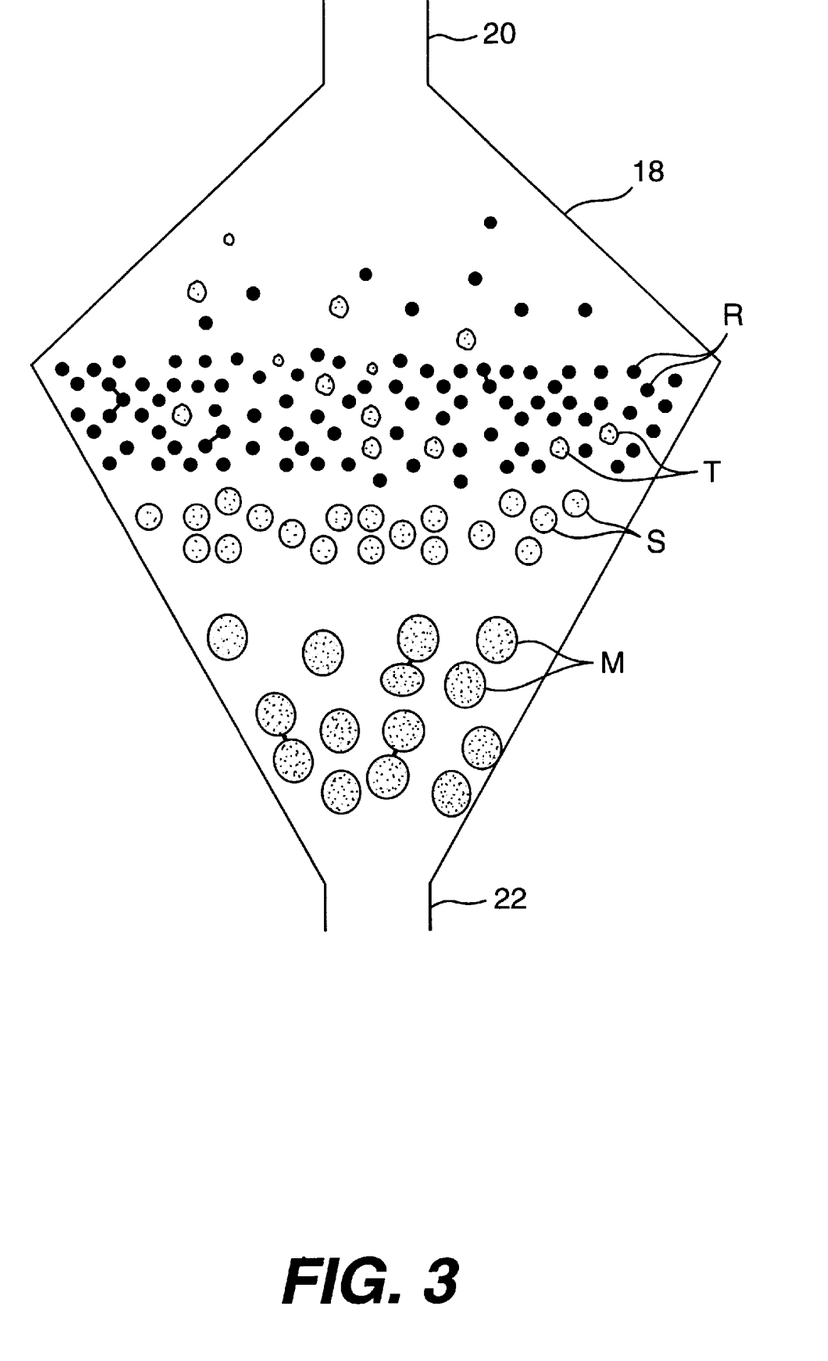
FIG. 3 is a schematic view of a saturated fluidized particle bed formed in the fluid chamber of FIG. 1 during a blood component separation procedure.

As shown in FIG. 3, plasma, diluting liquid, and any slower sedimenting platelets, flow through the saturated particle bed, while the particle bed retains relatively faster sedimenting stem cells "S" and tumor cells "M" in a portion of the fluid chamber 18 located between the bed and the fluid chamber inlet 22. The stem cells "S" reside just below the saturated fluidized bed and the faster sedimenting tumor cells "M" reside closer to the inlet 22. In addition to the stem cells "S," which normally express an antibody known as CD34+, the saturated fluidized particle bed may also retain all or a substantial number of other blood particles expressing the CD34+antibody, because these particles normally have similar sedimentation velocities. Some smaller stem cells "S" may reside in the saturated fluidized particle bed or flow through the bed along with the plasma and diluting liquid rather than residing below the bed.

As red blood cells "R" and T cells "T" continue to flow into the fluid chamber 18 and enter the saturated fluidized bed, the red blood cells "R" and T cells "T" flow from the outlet 20. Because the fluidized particle bed is saturated, the rate at which red blood cells and T cells "T" enter the inlet 22 equals the rate at which red blood cells "R" and T cells "T" pass through the outlet 20. The flow of red blood cells "R" and T cells "T" also carries with it some portion of the number of stem cells "S." Generally, a larger number of stem cells "S" exit the fluid chamber 18 when the starting number of red blood "R" cells and/or white blood cells is greater.

Since the diluting liquid has a density less than that of the plasma and other blood components flowing through the first conduit 28, the mixing of the diluting liquid and blood components in the three-way connector 34 lowers the overall density of the combined suspension of the liquids and particles in the fluid chamber 18. This reduces Coriolis jetting of the plasma and diluting liquid flowing through the fluid chamber 18 because the composite liquid has a density closer to that of the overall density of substances in the fluid chamber 18. In other words, making the overall density of substances in the fluid chamber 18 closer to the density of liquids entering the fluid chamber 18 reduces buoyancy forces tending to move the liquid toward the fluid chamber outlet 20.

In contrast, when the overall density of substances in the fluid chamber 18 is relatively high, buoyancy forces cause the lower density liquids to flow in a Coriolis jet along the fluid chamber's inner wall surface facing the direction of rotation of the rotor 12. This Coriolis jetting of the liquids carries faster sedimenting particles, such as the tumor cells "M," toward the fluid chamber outlet 20 and thereby allows these particles to flow from the fluid chamber 18 and to mix with the slower sedimenting particles, such as red blood cells, T cells, and stem cells. Because Coriolis jetting is reduced with the present invention, more of the faster sedimenting tumor cells "M" can be separated from the blood component particles.

Diluting the blood components with diluting liquid allows for the blood components in the first conduit 38 to be pumped into the fluid chamber 18 and separated at a faster, more constant flow rate while particles are entering the fluid chamber 18 and afterward while pure diluting liquid is entering the fluid chamber 18. In contrast, when the blood components are separated in the fluid chamber 18 without dilution, the viscosity and density of plasma do not allow such high flow rates. In addition, some of the tumor cells may be forced or carried through the fluid chamber outlet 20, due to high suspension densities in the chamber combined with the low density of pure diluting liquid following the last cells into the chamber 18.

During particle separation, the pumping of the blood components in the first conduit 28 and the pumping of the diluting liquid in the second conduit 30 are controlled so that the flow rate of diluting fluid exceeds the flow rate of blood components. For example, the ratio of the flow rate of diluting liquid to the flow rate of blood components is preferably from about 1 to about 20, more preferably from about 2 to about 8, and most preferably about 6. Highly diluting the blood components with the diluting liquid allows for separation of the tumor cells and blood particles at an increased flow rate.

Although the diluting liquid and blood components are preferably mixed in the three-way connector 34 during a particle separation procedure, other mixing configurations are possible. For example the fluid chamber 18 could be modified to include separate inlets for blood components and diluting liquid. In addition, the diluting liquid could be added only during certain portions of the separation process. The diluting liquid could also be added to the blood components in the first source 38 before, or at the beginning of, a separation procedure.

Eventually all of the blood components flow from the first source 38 to the fluid chamber 18, and the first source 38 reaches an empty state. Thereafter, a quantity of the diluting liquid alone is passed into the fluid chamber 18 to reduce the overall density of substances in the fluid chamber 18 even further and thereby reduce Coriolis jetting. For example, 250 ml of pure diluting liquid is passed into the fluid chamber 18 after the first source 38 is empty. The diluting liquid flushes some of the desired particles from the fluid chamber 18.

After the blood components become depleted from the first source 38, and diluting fluid has flushed a sufficient number of desired cells from the chamber 18, to further lower the suspension density in the chamber 18, the remaining stem cells "S" and other desired particles in the fluid chamber 18 are harvested. During harvesting, the flow rate of the diluting liquid is increased gradually in increments so that particles having relatively slower sedimentation velocities are flushed from the fluid chamber 18. The flow velocity of diluting liquid is preferably increased in a relatively slow and gradual fashion and at a relatively constant (linear) rate. Slowly increasing the flow rate of diluting liquid in this manner, reduces the likelihood of Coriolis jetting caused by sudden flow rate increases.

As harvesting continues, the flow rate of diluting liquid is increased until it is about 50% to about 100% greater than the combined flow rate of blood components and diluting liquid prior to harvesting, for example. Preferably, a fluidized bed of particles remains throughout a substantial portion of the harvesting. The reduced overall density of substances in the fluid chamber 18 reduces the likelihood of Coriolis jetting during particle harvesting. Preferably, the flow rate increase continues until just before tumor cells "M" start to emerge from the fluid chamber outlet 20.

The diluting liquid, plasma, red blood cells, T cells, stem cells, and any other materials flowing from the fluid chamber outlet 20 pass through the intermediate tubing 48 to the inlet 50 of the separation vessel 52. In the separation vessel 52, centrifugal force caused by rotation of the rotor 12 retains the particles in the collection well 54, while the diluting liquid and plasma flow through the liquid outlet 60 and liquid outlet line 62. This separates the red blood cells, stem cells, and other particles from the diluting liquid and plasma.

The particles and a portion of the liquids flow through the particle concentrate line 58 to one or more particle collection containers 70, and the diluting liquid and plasma flow through the liquid collection line 62 to the liquid collection container 66. After the first source 38 is empty, and desired cells have been recovered into collection containers 70, a procedurist terminates rotation of rotor 12 and optionally removes tumor cells and any other cells from the fluid chamber 18 for testing or other purposes.

When the blood components in the first source 38 and/or the diluting liquid in the second source 42 include the above-mentioned polymer having the chemical formula HO—(CH$_2$CH$_2$O)$_A$—(CHCH$_3$CH$_2$O)$_B$—(CH$_2$CH$_2$O)$_A$—H, the polymer reduces adherence of at least some of the particles, such as the red blood cells, T cells, and stem cells. In particular, the polymer reduces rouleau (linking) of the red blood cells to one another. This improves separation of the particles in the fluid chamber 18 because the individual particles do not adhere to one another or to the components of the system 10. Therefore, the use of the polymer increases the number of red blood cells, T cells, and or stem cells collected in the particle collection containers 70, especially when the first source 38 initially includes a small number of these particles.

In another aspect of the invention, the polymer can be used to improve particle separation when the particles are separated in the fluid chamber 18 according to differences in sedimentation velocity without forming a saturated fluidized particle bed in the fluid chamber 18. For example, the polymer can be used when particles are separated in the fluid chamber 18 by elutriation.

When the present invention is used to separate particles including red blood cells, the red blood cells act as individual, independent, sedimenting particles without significant rouleau of the red blood cells. The use of the diluting liquid reduces the density and viscosity of substances flowing in the fluid chamber 18, and thereby limits the occurrence of red blood cell rouleau. Adding the above-mentioned triblock copolymer to the substances flowing in the fluid chamber 18 also limits the tendency of red blood cell rouleau by reducing adhesion of red blood cells to one another. Because rouleau of the red blood cells is reduced, the red blood cells form at least part of the saturated fluidized particle bed rather than acting like faster sedimenting particles.

In the present invention, the red blood cells in the saturated bed block passage of faster sedimenting tumor cells. Because the bed forming red blood cells behave as if they have a faster sedimentation velocity than stem cells, the red blood cells permit stem cells to pass through the saturated bed. Stem cell recovery and tumor cell filtering are improved when large numbers of red blood cells are used. In contrast, in elutriation red blood cells are typically removed before the flow rate based separation.

It will be apparent to those skilled in the art that various modifications and variations can be made to the structure and methodology of the present invention without departing from the scope or spirit of the invention. For example, the present invention could be used to separate tumor cells from red blood cells, and the cell suspension in the first source 38 may not include T cells and/ or stem cells. In view of the foregoing, it is intended that the present invention cover modifications and variations of this invention provided they fall within the scope of the following claims and their equivalents.

What is claimed is:

1. A method of separating first particles and second particles having different sedimentation velocities, comprising:

rotating a fluid chamber about an axis of rotation;

passing, into the fluid chamber, a first liquid carrying the first and second particles;

forming, in the fluid chamber, a saturated fluidized bed including the first particles, to thereby retain the second particles in the fluid chamber;

flowing into the fluid chamber a second liquid, the second liquid having a density less than that of the first and second particles so that the second liquid reduces an overall density of substances separated in the fluid chamber and thereby limits Coriolis jetting of at least one of the first and second liquid in the fluid chamber, wherein the flowing of the second liquid includes flowing the second liquid into the fluid chamber when the saturated fluidized bed is in the fluid chamber; and allowing the first liquid, the second liquid, and at least a portion of the first particles to flow from the fluid chamber.

2. The method of claim 1, further comprising mixing the second liquid and the first liquid carrying the first and second particles.

3. The method of claim 1, further comprising flowing the first liquid, the second liquid, and the portion of first particles from the fluid chamber into a separation vessel, separating the first particles from the first and second liquid in the separation vessel, and collecting at least the first particles in a container.

4. The method of claim 1, wherein the first liquid includes plasma, the first particles include at least one of red blood cells, T cells, and stem cells, and the second particles include tumor cells, and wherein the first particles forming the saturated fluidized bed include at least the red blood cells.

5. The method of claim 4, wherein the second liquid is an electrolyte solution having a pH of from about 7.0 to about 7.8.

6. The method of claim 5, wherein the second liquid is saline solution having a pH of about 7.4.

7. The method of claim 4, further comprising increasing a flow rate of the second liquid into the fluid chamber so that stem cells are flushed from the fluid chamber, the reduced overall density of the substances in the fluid chamber limiting Coriolis jetting of the second liquid.

8. The method of claim 1, further comprising adding, to at least one of the first liquid and the second liquid, a polymer having the chemical formula $HO-(CH_2CH_2O)_A-(CHCH_3CH_2O)_B-(CH_2CH_2O)_A-H$, wherein A satisfies the expression $0 \leq A \leq 150$ and B satisfies the expression $0 \leq B \leq 100$.

9. The method of claim 8, wherein A satisfies the expression $75 \leq A \leq 76$ and B is 30.

10. A method of separating tumor cells from a cell suspension, comprising:

rotating a fluid chamber about an axis of rotation;

flowing a cell suspension including at least a first liquid, first cells, and tumor cells into the fluid chamber;

forming, in the fluid chamber, a saturated fluidized bed including at least the first cells, the saturated fluidized bed retaining tumor cells in the fluid chamber;

mixing a second liquid and the first liquid, the second liquid having a density less than that of the cell suspension so that the second liquid reduces overall density of substances separated in the fluid chamber and thereby limits Coriolis jetting of at least one of the first liquid and the second liquid in the fluid chamber, wherein the mixing includes mixing the first and second liquids when the saturated fluidized bed is in the fluid chamber; and allowing at least the first liquid, the second liquid, and at least a portion of the first cells to flow from the fluid chamber.

11. The method of claim 10, wherein the mixing precedes the flowing.

12. The method of claim 10, wherein the cell suspension includes at least plasma and stem cells, and wherein the method further comprises flowing the second liquid, plasma, and stem cells from the fluid chamber into a separation vessel, separating at least the stem cells from second liquid and plasma in the separation vessel, and collecting at least the stem cells in a container.

13. The method of claim 10, wherein the first cells include at least one of red blood cells and T cells, and wherein the forming includes establishing a saturated fluidized bed with at least one of the red blood cells and the T cells.

14. The method of claim 10, wherein the second liquid is an electrolyte solution having a pH of from about 7.0 to about 7.8.

15. The method of claim 14, wherein the second liquid is saline solution having a pH of about 7.4.

16. The method of claim 10, wherein the cell suspension includes at least stem cells, and wherein the method further comprises flushing stem cells from the fluid chamber with the second liquid, the reduced overall density of the substances in the fluid chamber limiting Coriolis jetting of the second liquid.

17. The method of claim 10, wherein the cell suspension comprises blood components, and wherein the method further comprises separating platelet rich plasma and red blood cells from peripheral blood to obtain the blood components.

18. The method of claim 10, wherein the cell suspension comprises blood components, and wherein the method further comprises separating platelet rich plasma and red blood cells from bone marrow blood to obtain the blood components.

19. A method of reducing particle adhesion in a particle separation procedure, comprising:

rotating a fluid chamber about an axis of rotation;

flowing liquid carrying particles into the fluid chamber;

separating particles in the fluid chamber according to differences in sedimentation velocity;

adding, to the liquid, a polymer having the chemical formula $HO-(CH_2CH_2O)_A-(CHCH_3CH_2O)_B-(CH_2CH_2O)_A-H$, wherein A satisfies the expression $0 \leq A \leq 150$ and B satisfies the expression $0 \leq B \leq 100$, the polymer reducing adherence of at least some of the particles to improve separation of the particles; and allowing at least some of the particles to flow from the fluid chamber.

20. The method of claim 19, wherein A satisfies the expression $75 \leq A \leq 76$ and B is 30.

21. The method of claim 19, wherein the separating includes forming a saturated fluidized bed of particles in the fluid chamber.

22. The method of claim 19, wherein the separating includes filtering the particles by elutriation.

23. The method of claim 1, wherein the liquid carrying first and second particles is a cell suspension and wherein the second particles include tumor cells.

24. The method of claim 1, wherein at least portions of the passing and the flowing are performed simultaneously.

25. The method of claim 2, wherein at least portions of the passing and the flowing are performed simultaneously.

26. The method of claim 1, wherein the flowing further includes flowing the second liquid into the fluid chamber after passing the first liquid into the fluid chamber.

27. The method of claim 1, wherein the flowing further includes flowing the second liquid into the fluid chamber before the saturated fluidized bed is formed in the fluid chamber.

28. The method of claim 1, wherein the flowing further includes flowing the second liquid into the fluid chamber during formation of the saturated fluidized bed in the fluid chamber.

29. The method of claim 10, wherein the mixing further includes mixing the first and second liquids before the saturated fluidized bed is formed in the fluid chamber.

30. The method of claim 10, wherein the mixing further includes mixing the first and second liquids during formation of the saturated fluidized bed in the fluid chamber.

* * * * *